US00PP28312P2

(12) United States Plant Patent
Ranney

(10) Patent No.: US PP28,312 P2
(45) Date of Patent: Aug. 22, 2017

(54) BEAUTYBERRY 'NCCX2'

(50) Latin Name: *Callicarpa*
Varietal Denomination: NCCX2

(71) Applicant: North Carolina State University, Raleigh, NC (US)

(72) Inventor: Thomas Green Ranney, Arden, NC (US)

(73) Assignee: NorthCarolina State University, Raleigh, NC (US)

( * ) Notice: Subject to any disclaimer, the term of this patent is extended or adjusted under 35 U.S.C. 154(b) by 0 days.

(21) Appl. No.: 14/999,181

(22) Filed: Apr. 8, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

PLUTO Plant Variety Database Mar. 2, 2017 p. 1.*

* cited by examiner

*Primary Examiner* — Annette Para
(74) *Attorney, Agent, or Firm* — Cassandra Bright

(57) ABSTRACT

'NCCX2' is a new cultivar of hybrid beautyberry with a compact habit, purple emerging and fall foliage and abundant pink-purple fruit in the fall.

2 Drawing Sheets

Latin name of the genus and species: The Latin name of the novel plant variety disclosed herein is *Callicarpa*.

Variety denomination: The inventive hybrid of *Callicarpa* disclosed herein has been given the varietal denomination 'NCCX2'.

BACKGROUND OF THE INVENTION

The present invention comprises a new and distinct variety of *Callicarpa*, hereinafter referred to by the cultivar name 'NCCX2'. This new beautyberry was developed and selected in Mills River, N.C. 'NCCX2' was grown from seed collected from an open-pollinated group of $F_1$ hybrid *Callicarpa* sp., NCSU H2007-128 (*Callicarpa kwangtungensis*×*Callicarpa dicotoma*. The first asexual propagation of 'NCCX2' was carried out in July 2012 by rooting stem cuttings at the North Carolina State University, Mountain Horticultural Crops Research Station, Mills River, N.C. and has been asexually reproduced repeatedly by vegetative cuttings over a four-year period. 'NCCX2' roots readily from softwood cuttings treated with a basal dip of 4,000-5,000 ppm indole butyric acid (potassium salt) in water. 'NCCX2' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. A compact, upright to rounded habit.
2. Purple young shoots and emerging leaves.
3. Green-purple fall foliage color.
4. Abundant pink-purple fruit in the fall.

BRIEF DESCRIPTION OF THE DRAWINGS

This new beautyberry is illustrated by the accompanying photographs which show the plant's form, foliage and fruit. The colors shown are as true as can be reasonably obtained by conventional photographic procedures. Colors in the photographs may differ slightly from the color values cited in the detailed botanical description, which accurately describe the colors of the new hybrid beautyberry.

DETAILED BOTANICAL DESCRIPTION

Figure 1:
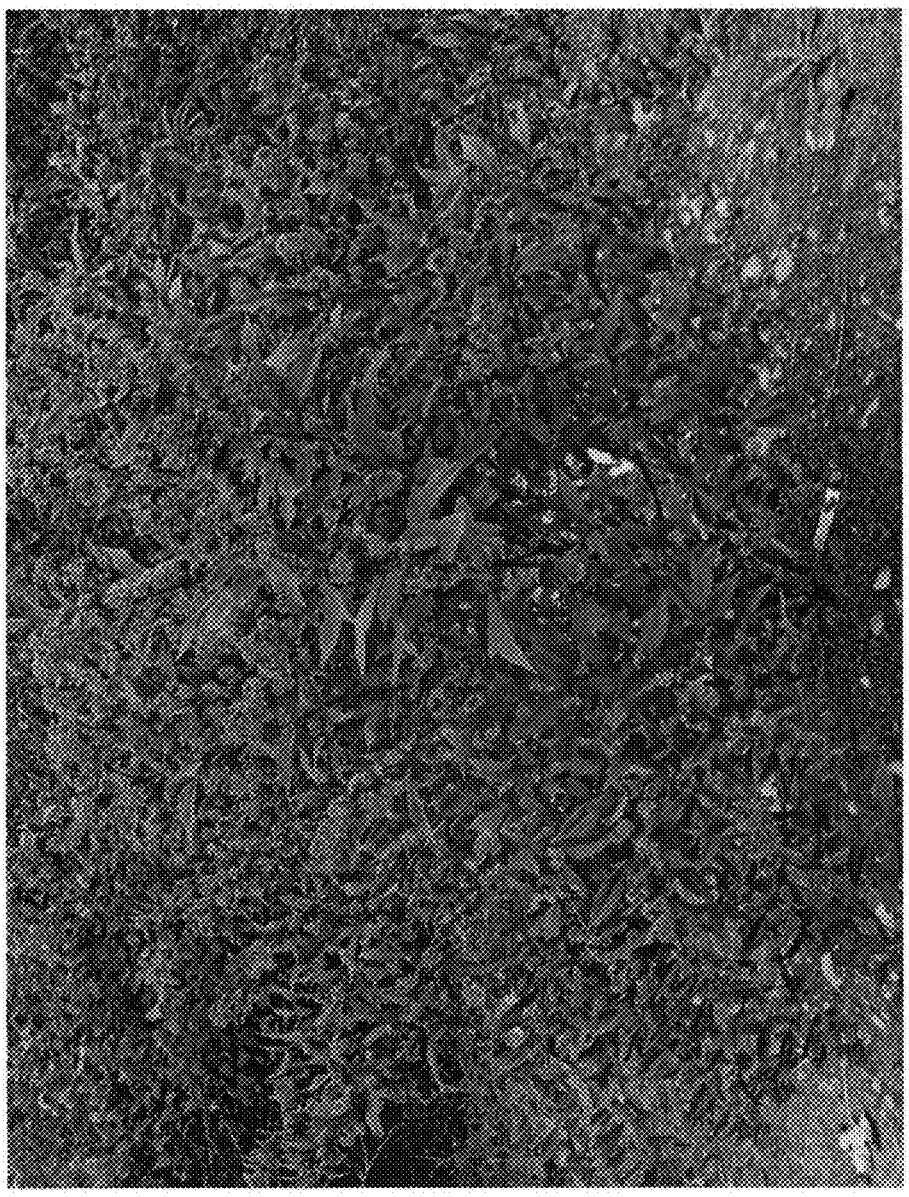
FIG. 1 is a color photograph showing the form, foliage, and fruit of 'NCCX2' on Sep. 28, 2015 on a five-year-old field-grown shrub.
Figure 2:
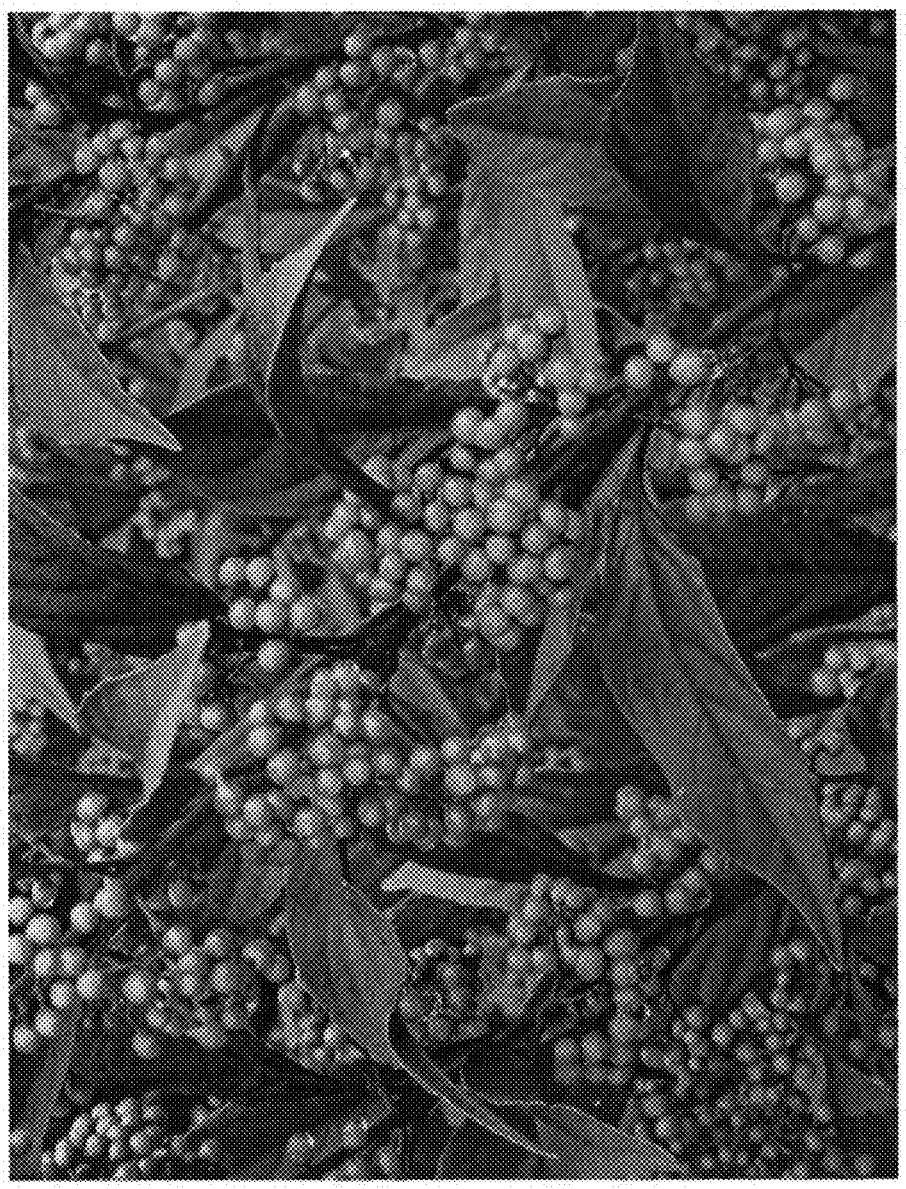
FIG. 2 is a color photograph showing the fruit of 'NCCX2' on Sep. 28, 2015 on a five-year-old field-grown shrub.

The following is a detailed description of the botanical characteristics of the new and distinct hybrid beautyberry variety plant known by the denomination 'NCCX2'. The detailed description was taken on a three-year-old field-grown plant in Mills River, N.C. in 2015. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Callicarpa* 'NCCX2'.
*Common name.*—Beautyberry.

Parentage: Seedling from open-pollinated group of $F_1$ hybrid *Callicarpa* sp., NCSU H2007-128 (*Callicarpa kwangtungensis*×*Callicarpa dicotoma*).

Plant description:

*Growth habit*.—Compact and upright, becoming more rounded with weight of maturing fruit.

*Height*.—Approximately 1 to 1.5 m at maturity.

*Width*.—Approximately 1 to 1.5 m at maturity.

Branch:

*Lateral branch length*.—Avg. 27.5 cm (range 11.0 to 50.0 cm).

*Lateral branch diameter*.—Avg. 0.3 cm (0.2 to 0.5 cm).

*Internode length*.—Avg. 4.8 cm (2.0 to 7.4 cm).

*Mature branch color*.—Greyed-Green (197B).

*Mature branch texture*.—Slightly pubescent.

*Immature branch color*.—Purple (N77A).

*Immature branch texture*.—Pubescent.

Leaves:

*Type*.—Simple.

*Arrangement*.—Opposite.

*Shape*.—Elliptic to ovate-lanceolate.

*Apex*.—Long acuminate.

*Base*.—Cuneate.

*Venation*.—Pinnate.

*Vein color, upper and lower*.—Red-Purple (59A).

*Vein texture*.—Pubescent.

*Margins*.—Serrate above middle.

*Emerging leaves*.—Color: Upper: Closest to Purple (N77A). Lower: Closest to Yellow-Green (148A). Texture: Pubescent.

*Mature leaves during growing season*.—Length of lamina: Avg. 8.9 cm (8.2 to 10.5 cm). Width: Avg. 2.8 cm (2.1 to 3.9 cm). Color: Upper: Yellow-Green (147A). Lower: Yellow-Green (147B). Texture: Sparsely pubescent.

*Fall foliage color*.—Green-purple [ranging from and including green (147A/B) on shaded leaves (both upper and lower surfaces) to dark purple (79A), particularly on upper side of leaves exposed to full sun].

*Leaf attachment*.—Petiolate.

*Petiole*.—Length: Avg. 0.5 cm (0.3 to 0.8 cm). Diameter: About 0.1 cm. Color: Red-Purple (59A). Texture: Sparsely pubescent.

Inflorescence:

*Flowering season*.—Beginning in June and lasting until October in Mills River, N.C.

*Inflorescence type*.—Cyme.

*Inflorescence diameter*.—Avg. 3.2 cm (3.0 to 3.5 cm).

*Inflorescence height*.—Avg. 2.4 cm (2.0 to 3.0 cm).

*Number of flowers per inflorescence*.—Avg. 23 flowers (21 to 29 flowers).

*Fragrance*.—None.

*Self-cleaning or persistent*.—Self-cleaning.

*Bud*.—Shape: Oblong. Length: About 0.3 cm. Diameter: About 0.1 cm. Color: White (N155B).

*Perianth*.—Diameter at antithesis: About 0.2 cm.

*Petal*.—Number: 4. Shape: Campanulate. Apex: Acute. Base: Fused. Margin: Entire. Length: About 0.3 cm. Width: About 0.2 cm. Color at maturity, upper and lower: White (N155B). Texture: Smooth.

*Sepal*.—Number: 4. Shape: Funnel-form. Apex: Abruptly acute. Base: Fused. Margin: Entire above fused region. Length: About 0.2 cm. Width: About 0.2 cm. Color, upper and lower: Red-purple (59A). Texture: Smooth.

*Peduncle*.—Length: Avg. 0.9 cm (0.7 to 1.1 cm). Width: About 0.1 cm. Color: Purple (N77A). Texture: Pubescent.

*Bracteoles*.—Number per inflorescence: 2 to 10. Length: About 0.2 cm. Width: Less than 0.1 cm. Color: Purple (N77A).

Reproductive organs:

*Gynoecium*.—Pistil number: 1. Pistil length: About 0.6 cm. Style length: About 0.5 cm. Style color: White (155C).

*Androecium*.—Stamen number: 4. Stamen length: About 0.3 cm. Stamen width: About 0.1 cm. Pollen color: Yellow (9C).

*Fruit and seed*.—Fruit type: Berry-like drupe. Fruit shape: Globose. Frit diameter: 0.25 cm (0.2 to 0.3 cm). Fruit color: Pink-purple (ranging from and including N74C to N78A). Fruit texture: Glabrous, shiny. Seed color: Yellow-orange (18B). Seed shape: Ovoid, flattened. Seed length: About 0.2 cm. Seed width: About 0.15 cm. Seed texture: Glabrous.

Disease and insect resistance: No significant disease or insect pests have been observed.

Cold hardiness: At least USDA zone 6b; testing has not been completed in colder zones.

COMPARISON WITH COMMERCIAL CULTIVARS

'NCCX2' is distinguished from *Callicarpa* 'NCCX1' in that 'NCCX2' has a smaller, more compact form of 1.0 to 1.5 m tall and wide, whereas *Callicarpa* 'NCCX1' will grow larger than 2.0 m tall and wide. 'NCCX2' is distinguished from *Callicarpa dichotoma* 'Issai' (unpatented) in that 'NCCX2' has purple new shoots, emerging leaves, and fall foliage color, whereas 'Isaai' has green shoots and foliage throughout the growing season.

What is claimed is:

1. A new and distinct hybrid beautyberry plant named 'NCCX2' substantially as illustrated and described herein.

* * * * *